United States Patent
Lederer

(10) Patent No.: US 7,609,844 B2
(45) Date of Patent: Oct. 27, 2009

(54) NOISE ATTENUATING HEADSET

(76) Inventor: Wayne Lederer, 1995 Park St., Atlantic Beach, NY (US) 11509

(*) Notice: Subject to any disclaimer, the term of this patent is extended or adjusted under 35 U.S.C. 154(b) by 44 days.

(21) Appl. No.: 11/851,860

(22) Filed: Sep. 7, 2007

(65) Prior Publication Data

US 2008/0013775 A1    Jan. 17, 2008

Related U.S. Application Data

(62) Division of application No. 10/723,774, filed on Nov. 26, 2003, now Pat. No. 7,292,704.

(60) Provisional application No. 60/514,796, filed on Oct. 27, 2003, provisional application No. 60/514,802, filed on Oct. 27, 2003, provisional application No. 60/515,041, filed on Oct. 28, 2003, provisional application No. 60/516,482, filed on Oct. 31, 2003.

(51) Int. Cl.
*H04R 25/00* (2006.01)

(52) U.S. Cl. .................... 381/380; 381/382

(58) Field of Classification Search .......... 381/311, 381/328, 380, 382, 67, 334; 181/129, 130, 181/131; 600/410, 418, 421, 424, 427
See application file for complete search history.

(56) References Cited

U.S. PATENT DOCUMENTS

| | | | | |
|---|---|---|---|---|
| 3,539,031 A * | 11/1970 | Scanlon | ........................ | 181/129 |
| 3,730,290 A * | 5/1973 | Scanlon | ........................ | 181/135 |
| 3,790,712 A * | 2/1974 | Andries | ........................ | 381/67 |
| 4,302,635 A | 11/1981 | Jacobsen et al. | | |
| 4,701,952 A | 10/1987 | Taylor | | |
| 4,933,981 A | 6/1990 | Lederer | | |
| 5,277,184 A | 1/1994 | Messana | | |
| 5,313,945 A * | 5/1994 | Friedlander | ........................ | 600/410 |
| 5,412,419 A * | 5/1995 | Ziarati | ........................ | 348/61 |
| 5,427,102 A | 6/1995 | Shimode et al. | | |
| 5,539,831 A * | 7/1996 | Harley | ........................ | 381/67 |
| 5,627,902 A * | 5/1997 | Ziarati | ........................ | 381/385 |
| 5,821,748 A | 10/1998 | Gatehouse | | |
| 5,990,680 A | 11/1999 | Mansfield | | |
| 6,463,316 B1 | 10/2002 | Brungart | | |
| 6,466,681 B1 | 10/2002 | Siska et al. | | |
| 6,741,719 B1 * | 5/2004 | Orten | ........................ | 381/380 |
| 7,292,704 B2 * | 11/2007 | Lederer | ........................ | 381/380 |
| 2006/0123527 A1 | 6/2006 | Porzelt et al. | | |

OTHER PUBLICATIONS

Skopec, M., "A Primer on Medical Device Interactions with Magnetic Resonance Imaging Systems," U.S. Food and Drug Administration (http://www.fda.gov/cdrh/ode/primer16.html), CDRH pp. 1-16, 1997.

* cited by examiner

*Primary Examiner*—Curtis Kuntz
*Assistant Examiner*—Phylesha Dabney
(74) *Attorney, Agent, or Firm*—Fish & Richardson P.C.

(57) ABSTRACT

Systems and techniques are disclosed for a headset that may be used in an audio system used in a magnetic field. In one aspect, the system includes an inner set portion adapted to fit into an ear canal. A pneumatic port is disposed in the hole to couple audible sounds to the ear canal. The system may include a non-magnetic transducer coupled to the pneumatic port. The system also may include a fiber-optic microphone to couple sound from a user of the headset. Other techniques provide a stethoscope-type yoke to couple the pneumatic port and the fiber-optic antenna to the non-magnetic transducer.

8 Claims, 4 Drawing Sheets

NOISE ATTENUATING HEADSET

CROSS REFERENCE TO RELATED APPLICATIONS

This application is a divisional of U.S. Ser. No. 10/723,774, filed on Nov. 26, 2003, which in turn claims the benefit of priority from U.S. Provisional Application No. 60/514,482 filed Oct. 31, 2003; U.S. Provisional Application No. 60/515,041, filed Oct. 28, 2003; U.S. Provisional Application No. 60/514,802, filed Oct. 27, 2003; and U.S. Provisional Application No. 60/514,796, filed Oct. 27, 2003 all of which are incorporated herein by reference in their entirety.

BACKGROUND

This disclosure relates to noise-attenuating headsets for use in magnetic fields. Magnetic resonance imaging systems (MRI) produce loud noises associated with the drive pulses applied to the gradient coils. As MRI technology has advanced and the gradient coils have become more powerful, the level of the sound produced has increased to a point where it may be necessary to provide sound pressure protection for people in the vicinity of the MRI system when the system is operating.

SUMMARY

The present application describes systems and techniques relating to noise reduction headsets in a magnetic environment.

The technique includes a magnetically inert headset comprising an outer set portion disposed in an ear cup adapted to cover an ear. An ear insert having a through-hole is disposed in the outer set portion, wherein the inner set portion is adapted to fit into an ear canal. A pneumatic port is disposed in the hole in the inner set to couple audible sound waves to the ear canal.

In an implementation, the technique is facilitated by including a stethoscope-type yoke to couple the pneumatic port to a non-magnetic audio transducer.

In another implementation, the technique is facilitated by including a non-magnetic microphone to enable a user of the headset to communicate with another person. The non-magnetic microphone may be a fiber-optic microphone or a piezoelectric microphone.

In another aspect, the technique includes inserting an ear insert having a through-hole into a ear canal of a user; disposing a pneumatic port into the hole in the ear insert; coupling the pneumatic port to a pneumatic tube; and coupling the pneumatic tube to an output of an audio transducer.

Some implementations of the systems and techniques described herein may provide one or more of the following advantages. The system may reduce the sound level due to the operation of a magnetic device such as a magnetic resource imaging system from entering a user's ear canal. The technique may enable communication to a user in a noisy environment and, in some implementations, enable the user to communicate with another person.

Details of one or more implementations are set forth in the accompanying drawings and the description below. Other features and advantages may be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

The systems and techniques disclosed here relate a system for reducing noise in a headset used in a magnetic environment. For example, MRI systems can produce loud noises associated with drive pulses applied to the MRI gradient coils. A headset may be used to decrease the level of sound that a person hears while undergoing examination in, or in the vicinity of, the MRI system when the system is operating. The headset also may enable a user, such as a patient undergoing an MRI examination, to hear a MRI technologist while the MRI system is operating. The headset can be made of non-magnetic materials and includes an ear insert that may be inserted into an ear canal to reduce the sounds heard by the user.

Figure 1A:
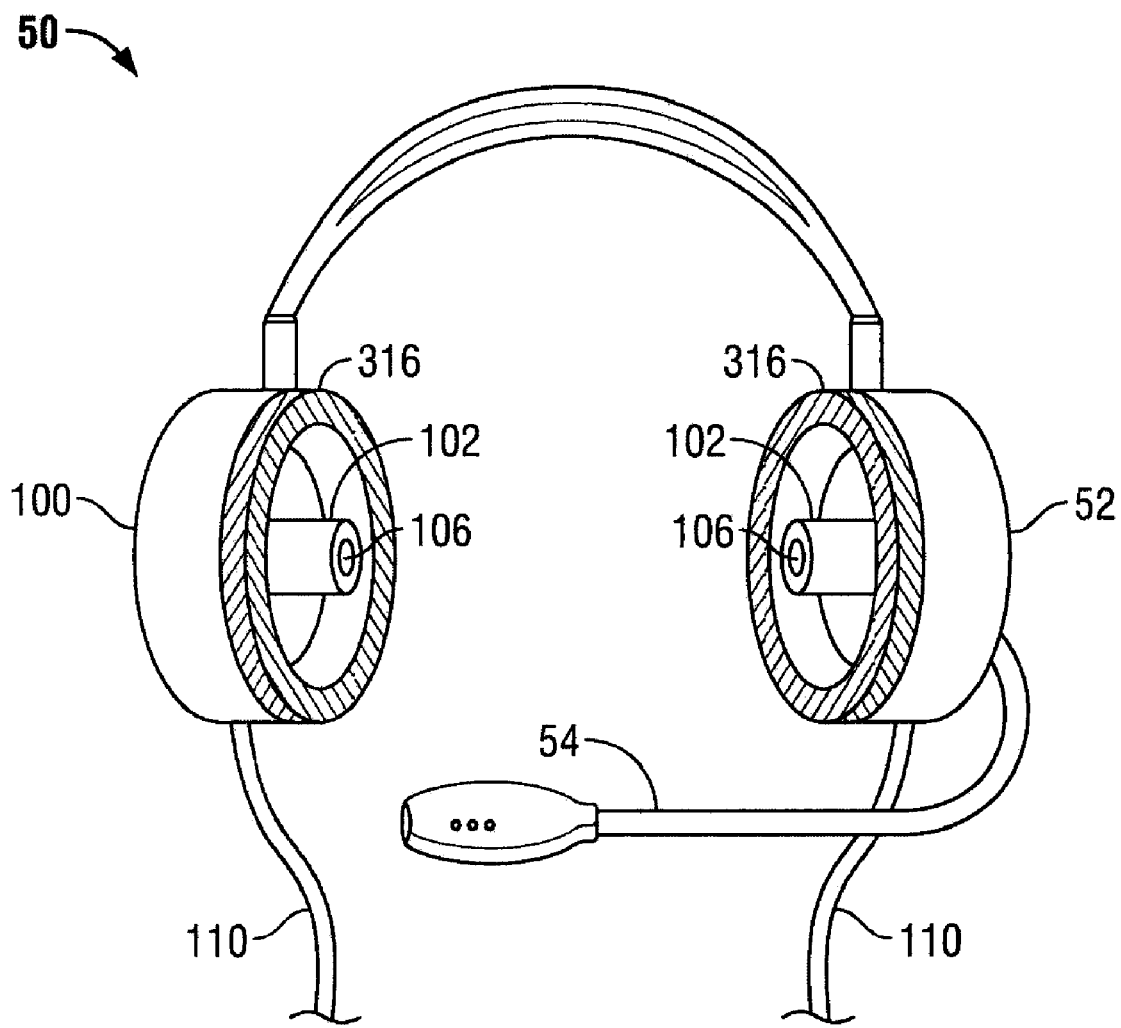
FIGS. 1A-B are illustrations of a first embodiment of the disclosed technique.

FIG. 1A illustrates a noise-attenuating headset 50. The headset includes right and left ear covers 100, 52, respectively, which may have foam padding 316 to attenuate noise and cushion the ear covers when in use. A respective ear insert 102 is disposed in each ear cover. The ear insert is adapted to fit into an ear canal of a user. The ear insert may include a pneumatic port 106 to couple sound received through pneumatic tubes 110. A non-magnetic microphone 54 may be provided for on the headset. The microphone may be used to permit a user to communicate with another person.

Figure 1B:
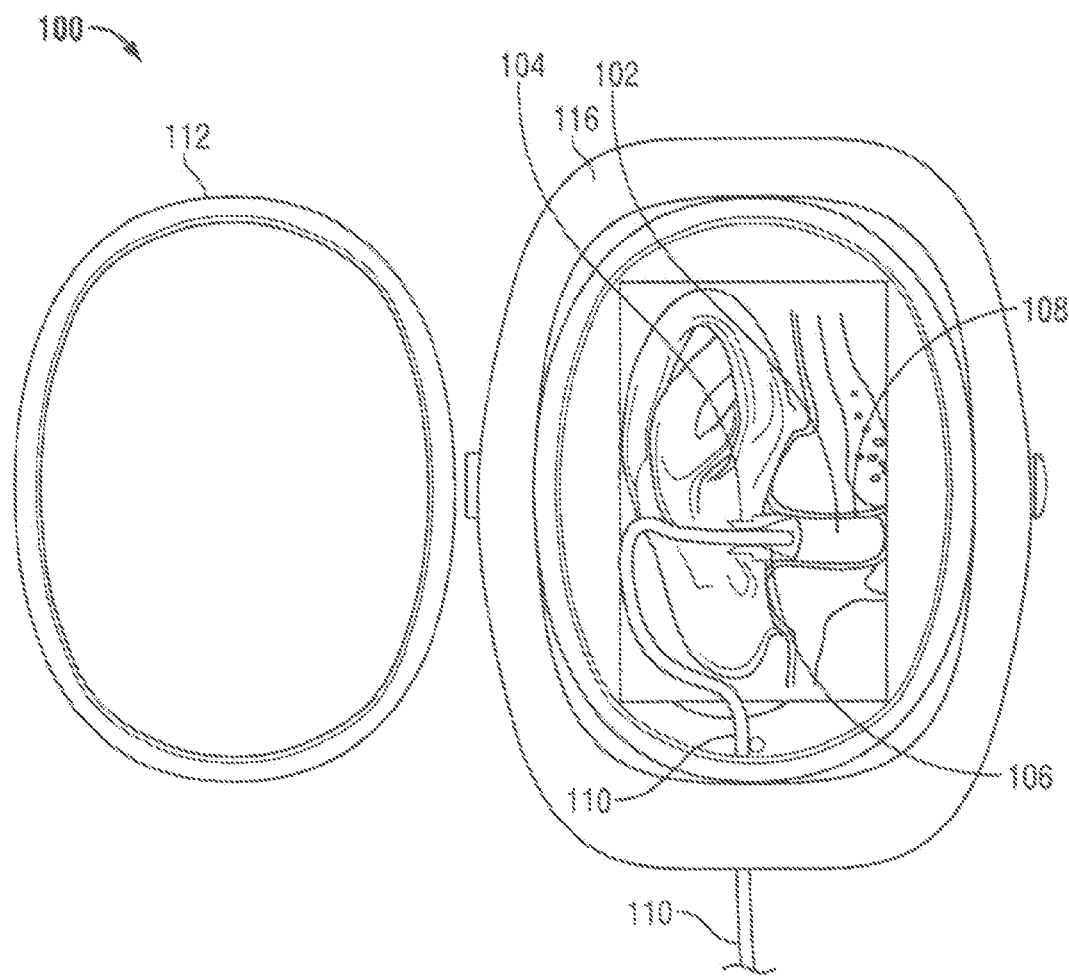

FIG. 1B illustrates the right-side ear cover 100. The left-side may be similarly structured. The headset may be made of non-magnetic materials that are not affected by a magnetic field. The headset includes an inner set portion that may include the ear insert 102 and the pneumatic port 106. The ear insert is adapted to fit into a person's ear canal 108. In an implementation, the ear insert may be made of a material that can conform to the shape of the ear canal upon insertion therein such as compressible foam, vinyl, plastic or rubber. The ear insert may be made in alternative sizes, shapes or materials to conform to the variations in ear canal geometry of different users. Placing the insert within the ear canal so that it substantially conforms to the shape of the ear canal can attenuate the noises that may be created by the gradient coils of a MRI system. An adapter 104 may be used to support the pneumatic port and can couple the port to pneumatic tubing 110. The pneumatic tubing 110 can be used to carry sounds from the output of an audio transducer (not shown). The inner set portion may be disposed within an outer set portion, which includes an ear cup 116. The ear cup 116 may come in different sizes to accommodate different sizes of ears. In an implementation, the ear cup 116 may be provided with a removable access piece 112 to provide access to the inner set portion through an outer surface of the ear cup 116.

Figure 2:
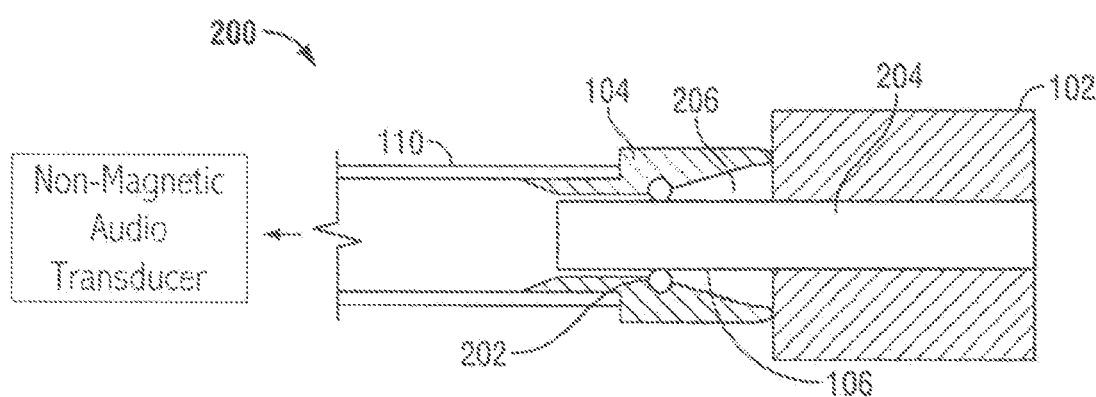
FIG. 2 is an implementation of an inner set portion.

FIG. 2 illustrates an implementation of an inner set portion 200 comprising the ear insert 102 and the pneumatic port 106. The ear insert 102 has a through-hole 204. The pneumatic port 106 may be in the form of a hollow tube and disposed within the ear insert hole 204. The pneumatic port 106 can provide coupling of sound to the ear canal without substantially disturbing the contact between the ear insert and ear canal walls. In an implementation, the ear insert 102 may be intended for disposal after each use for various reasons such as for sanitary purposes. The adapter 104 may be used to couple the pneumatic port 106 to the pneumatic tube 110. In an implementation, the adapter may have a conical opening 206 to help guide the pneumatic port 106 into the pneumatic tube 110. The adapter may comprise a gasket 202 such as an O-ring disposed in the adapter to support, retain or help seal the pneumatic port 106 in the adapter 104.

In an implementation, a non-magnetic microphone may be coupled to the headset to enable communication between the headset wearer and another person. For example, in a MRI system, a user may wear the headset and communicate with the system operator. Non-magnetic microphones include noise-canceling fiber-optic and piezoelectric microphones. The microphone may be coupled to the headset by a non-magnetic mount. An optical fiber associated with the microphone may be routed adjacent the pneumatic tubes to provide connection to the microphone.

The pneumatic port 106 may be placed in the hole 204 of the ear insert 102. A first end of the pneumatic tubing 110 may be coupled to the pneumatic port 106. A second end of the pneumatic tubing may be coupled the output of an audio transducer (not shown). The audio transducer may be located in the magnet room of a MRI system. The ear insert 102 may be disposed in the ear canal. In an implementation, there is an adapter 104 having a conical opening on a first end. The conical adapter is disposed within the ear cup 116 such that when the headset is placed over the ears, the conical opening guides the pneumatic port 106 into the pneumatic tubing 110. The integrity of the coupling of the pneumatic port through the conical adapter to the pneumatic tubing 110 may be verified through the removable access piece 112. The removable piece then may be closed to help keep unwanted noise from the ear.

Figure 3:
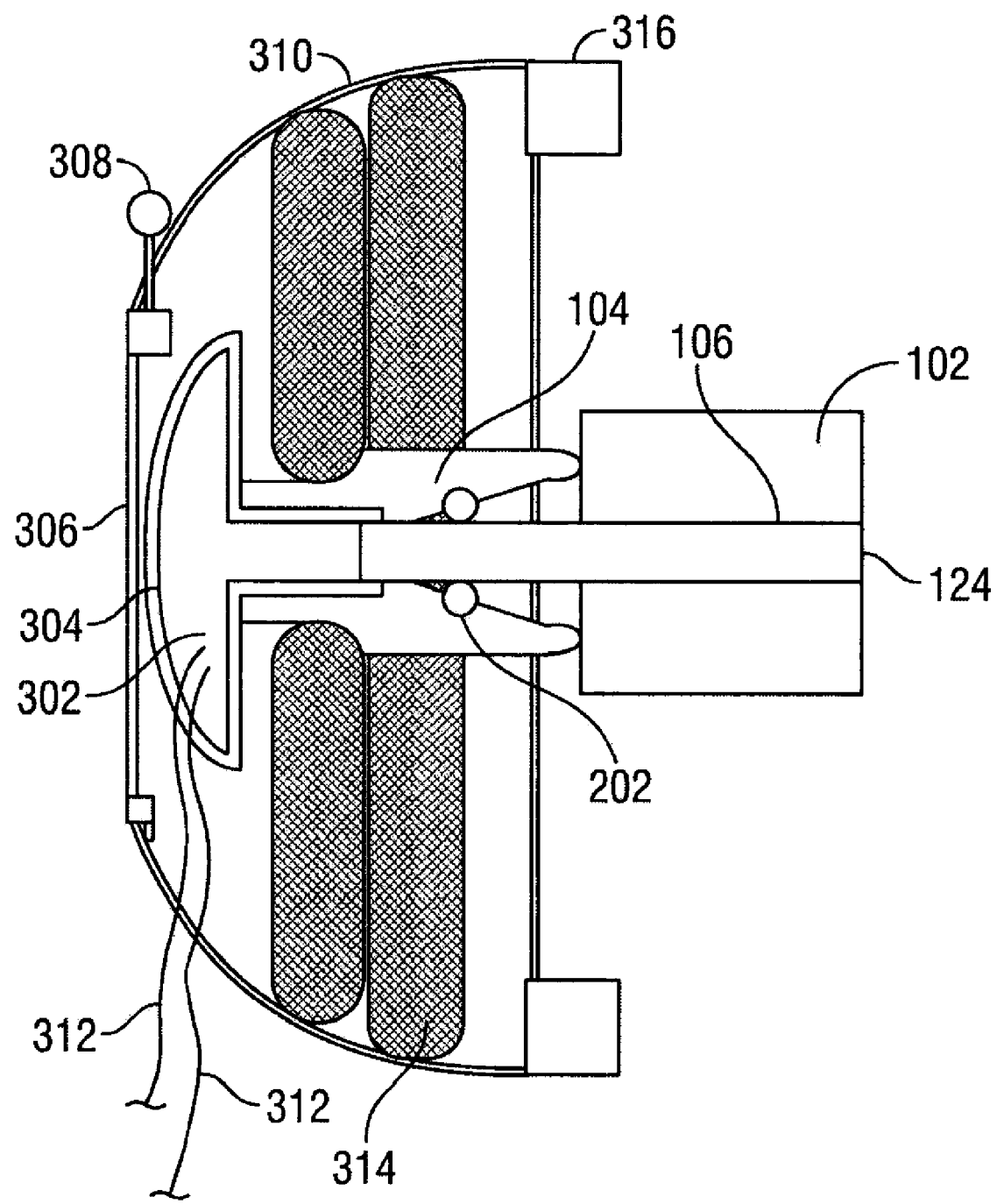
FIG. 3 is an implementation of the noise attenuation technique with a piezoelectric transducer.

FIG. 3 illustrates an implementation of the noise attenuating technique using a piezoelectric transducer. Previously described features will only be repeated as necessary. An ear cup 310 is adapted to fit over an ear. A pad 316 is attached to the ear cup to provide a cushion for the user of the headset and to help dampen sounds. The cushion may be made, for example, of a foam material. A sound absorbing foam 314 may be disposed inside the ear cup 310. A piezoelectric transducer includes a piezoelectric substrate 302 disposed in a piezoelectric enclosure 304. The audio output of an audio transducer (not shown) may be coupled by wires 312 to the piezoelectric transducer, which, in turn, may couple the audio output to the pneumatic port 106 and then through the ear insert that is inserted into the ear canal. The adapter 104 can be used to retain both the pneumatic port and the piezoelectric transducer in proximity with one another. In an implementation, a removable access piece 306 can provide an opening in the ear cup to provide access to the piezoelectric transducer 306, adapter 104, pneumatic port 106 and ear insert 102.

Figure 4:
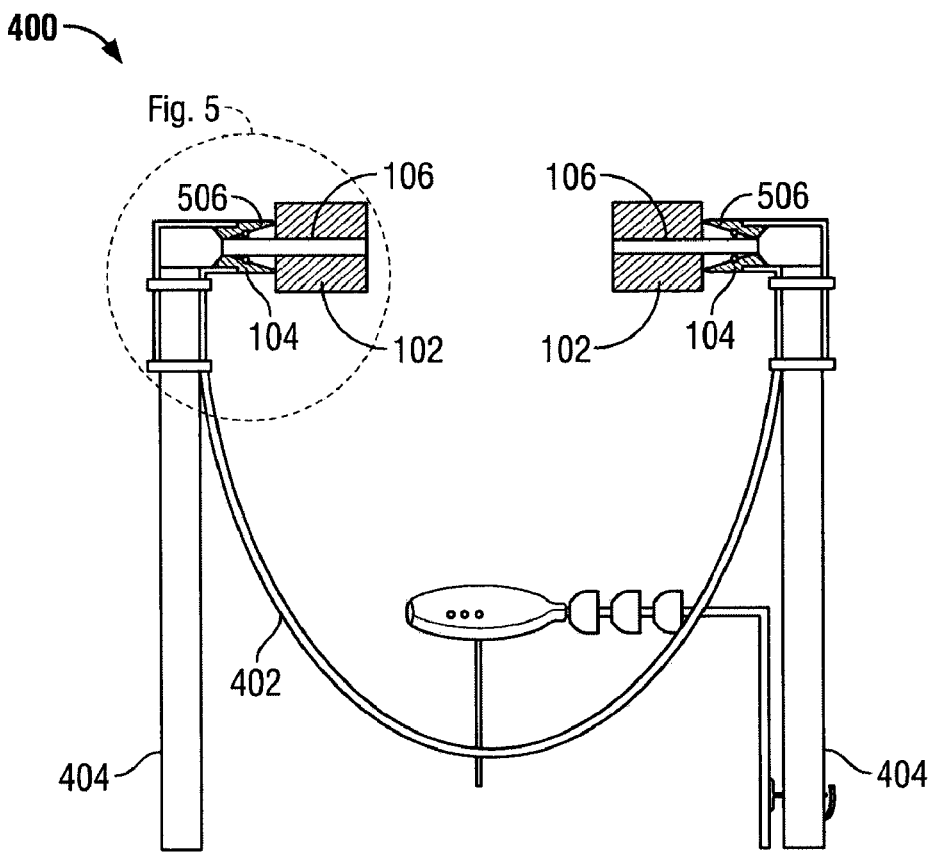
FIG. 4 is an implementation of the noise attenuation technique in a stethoscope-type headset.

FIG. 4 is an implementation of the noise attenuating technique in a stethoscope-type headset assembly 400. As described above, ear inserts 102 are inserted into the ear canal. The stethoscope-type assembly, through pneumatic tubing 404, couples output sounds from an audio transducer (not shown) to the pneumatic ports 106. A stethoscope tubing support 402 may hold the pneumatic tubes 404 together and may be made of a semi-rigid material that can provide a spring pressure to urge the ear inserts 102 into the ear canal. Ear inserts 102 have a through-hole and are adapted to fit into an ear canal. The pneumatic port 106 is disposed in the through-hole. Adapters 506 may be used to guide the pneumatic ports 106 into the pneumatic tubes 404. The stethoscope assembly may protrude from the user's head less than a headset using an ear cup. This type of assembly may be appropriate for users having a large head or ears that do not fit in available ear cups.

Figure 5:
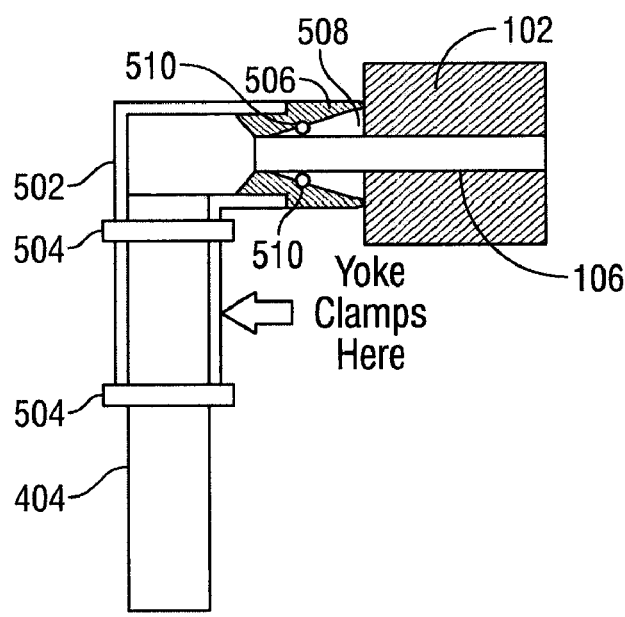
FIG. 5 is a detail view of the yoke attachment of the stethoscope-type headset of FIG. 4.

FIG. 5 is a detail view of the attachment of the pneumatic tube 404 to the pneumatic port 106. The adapter 506 may be used to couple the pneumatic port 106 to the pneumatic tube 404. In an implementation, the adapter may have a conical opening on a first end 508 to help guide and support the pneumatic port 106 into a yoke connector 502. The adapter may comprise a gasket 510 such as an O-ring disposed in the adapter to support, retain or help seal the pneumatic port 106 in the adapter 506. A second end of the adapter 506 is sized to fit snugly into a first end of the yoke connector 502 so as to reduce sound losses in the connection. Other connection arrangements may be used. The yoke connector 502 has a right-angle bend so as to reduce the distance that the stethoscope-type headset protrudes from the user's head. The pneumatic tube 404 is coupled into a second end of the yoke connector 502 such that sounds carried by the pneumatic tube 404 are coupled to the pneumatic port 106. Yoke clamps 504 may be used to secure the pneumatic tube 404 in the yoke connector 502.

The ear inserts 102 with the pneumatic ports 106 are inserted into the ear canals of the user. The adapter 506 may be inserted into the first end of the yoke connector 502 and the pneumatic tube 404 connected to the second end of the yoke connector and secured by the yoke clamps 504. The adapter/yoke connector assembly may then be positioned onto the pneumatic port 106.

Other embodiments are within the scope of the following claims.

What is claimed is:

1. A magnetically inert headset comprising:
   an ear insert having a through-hole and adapted to fit into an ear canal;
   a pneumatic port disposed in the hole in the ear insert to receive audible sound waves and couple the sound waves to the ear canal;
   a non-magnetic microphone coupled to the headset; and
   a stethoscope-type yoke, wherein the yoke includes pneumatic tubing acoustically coupled to both the pneumatic port and a non-magnetic transducer to couple the audible sound waves from the non-magnetic transducer.

2. The headset of claim 1 wherein the non-magnetic transducer comprises an audio transducer disposed in a magnet room of a magnetic resonance imaging system.

3. The headset of claim 1 wherein the non-magnetic transducer comprises a piezoelectric transducer.

4. The headset of claim 1 wherein the non-magnetic transducer comprises an electrostatic transducer.

5. A magnetically inert headset comprising:
   an ear insert having a through-hole and adapted to fit into an ear canal;
   a pneumatic port disposed in the hole in the ear insert to receive audible sound waves and couple the sound waves to the ear canal; and
   a stethoscope-type yoke, wherein the yoke includes pneumatic tubing acoustically coupled to both the pneumatic port and a non-magnetic transducer to coupled the audible sound waves from the non-magnetic transducer.

6. The headset of claim 5 wherein the non-magnetic transducer comprises an audio transducer disposed in a magnet room of a magnetic resonance imaging system.

7. The headset of claim 5 wherein the non-magnetic transducer comprises a piezoelectric transducer.

8. The headset of claim 5 wherein the non-magnetic transducer comprises an electrostatic transducer.

* * * * *

UNITED STATES PATENT AND TRADEMARK OFFICE
CERTIFICATE OF CORRECTION

PATENT NO.          : 7,609,844 B2                                    Page 1 of 1
APPLICATION NO.     : 11/851860
DATED               : October 27, 2009
INVENTOR(S)         : Wayne Lederer It is certified that error appears in the above-identified patent and that said Letters Patent is hereby corrected as shown below:

Column 4, Line 55, Claim 5, delete "coupled" and insert --couple--.

Signed and Sealed this

Twenty-third Day of February, 2010

David J. Kappos
*Director of the United States Patent and Trademark Office*